United States Patent [19]

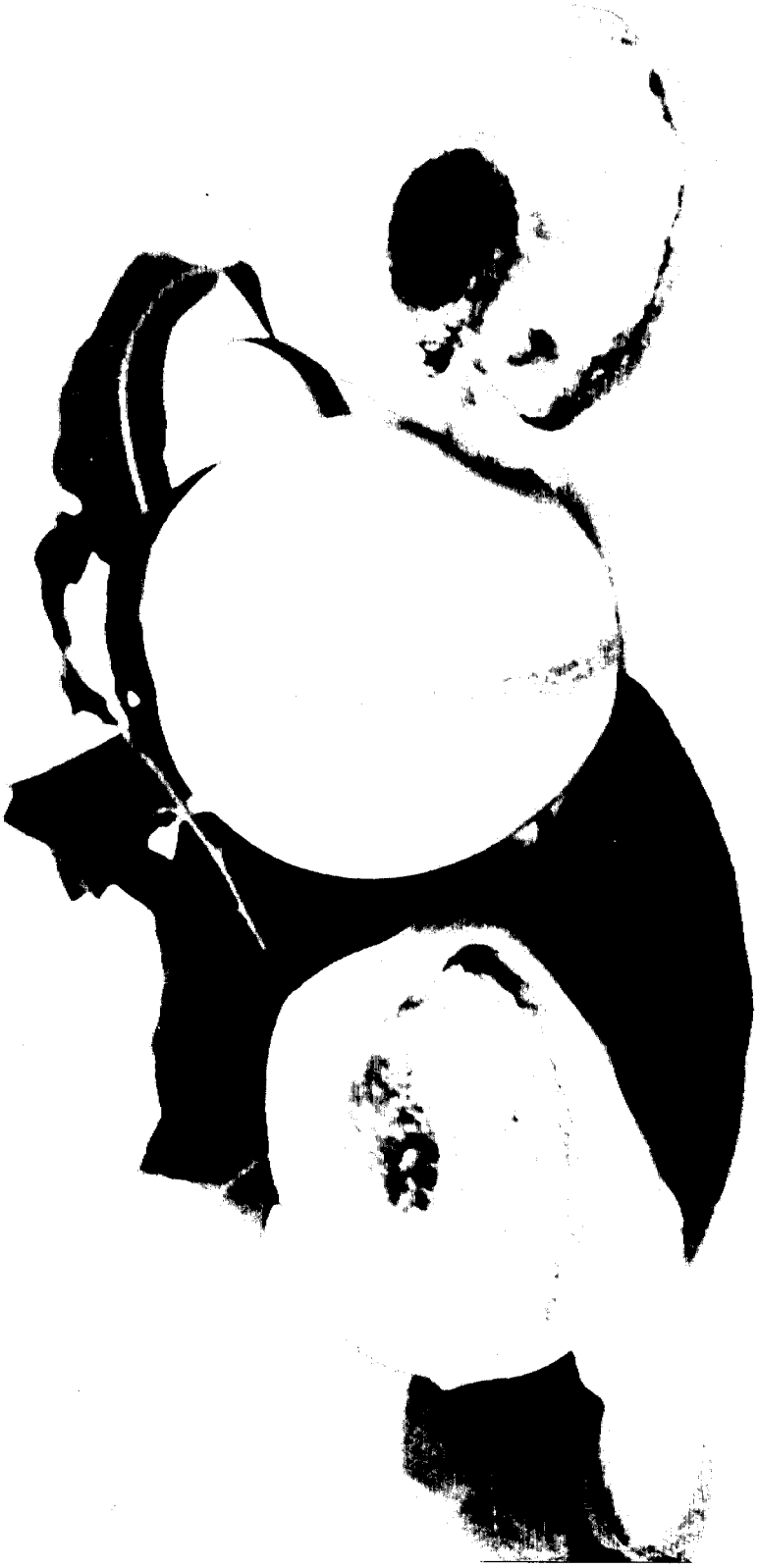

Pampaian

[11] Patent Number: Plant 5,581

[45] Date of Patent: Nov. 12, 1985

[54] PEACH TREE, PAMPAIAN'S LATE BABCOCK

[76] Inventor: James H. Pampaian, 6489 S. Alta Ave., Reedley, Calif. 93654

[21] Appl. No.: 581,182

[22] Filed: Feb. 17, 1984

[51] Int. Cl.[4] ..... A01H 5/03

[52] U.S. Cl. ..... Plt./42

[58] Field of Search ..... Plt./42

*Primary Examiner*—Robert E. Bagwill

*Attorney, Agent, or Firm*—Huebner & Worrel

[57] ABSTRACT

A new and distinct peach tree denominated as "Pampaian's Late Babcock" generally resembling the Giant Babcock Peach Tree (U.S. Plant Pat. No. 11,353) but bearing fruit ripening about one month later and having a distinctly-colored, roughly-textured suture line.

1 Drawing Figure

BACKGROUND OF THE NEW VARIETY

The present invention relates to a new and distinct variety of peach tree denominated varietally as "Pampaian's Late Babcock" and which is generally similar to the Giant Babcock Peach Tree (U.S. Plant Pat. No. 1,353) of which it is a sport but from which it is distinguished as to novelty by its bearing of fruit which ripens approximately one month later and has a distinctive suture line readily distinguishable from the surrounding skin coloration.

The Giant Babcock Peach Tree is well known as a vigorous producer of large, predominantly red-skinned fruit having ivory, freestone flesh streaked outwardly from the stone with shades of red and maturing in mid-July. Further, the fruit of the Giant Babcock Peach Tree has long been known as having a good eating quality and sweet flavor.

Therefore, it has long been recognized that it would be desirable to have a peach tree generally resembling the Giant Babcock, but which bears fruit later in the season, whereby the commercial demand for large, white-fleshed peaches can effectively be satisfied over a greater period of time.

ORIGIN AND ASEXUAL REPRODUCTION OF THE NEW VARIETY

For approximately twenty-five years, I have searched my own orchards of peach trees in an attempt to locate a late-ripening peach having white flesh. In 1981, during such a search, I was successful in discovering several peaches on a single limb of a Giant Babcock Peach Tree (U.S. Plant Pat. No. 1,353) in an orchard owned by me located at the corner of Alta and Clayton Avenues, near the City of Reedley, in the County of Fresno, in the State of California.

I asexually reproduced the new variety by budding it onto a Lovell Peach Tree in the same orchard in 1981. The fruit and tree characteristics resulting from such budding proved identical to those of the original sport.

SUMMARY OF THE NEW VARIETY

The instant variety of peach tree is characterized by perpetuating many of the desirable characteristics of the Giant Babcock Peach Tree, but has the important distinctions of bearing fruit ripening approximately one month later than that of the Giant Babcock. The suture line is dark red in coloration and the white flesh of the fruit has a red coloration radiating therethrough from the suture line toward the center of the fruit. The flesh of the fruit is of a firmer texture than that of the Giant Babcock, and is borne on a slightly longer stem which makes it possible for the fruit to remain on the tree longer and thus achieve improved ripening characteristics.

The tree of the instant variety is a vigorous, productive and regular bearer of fruit having an average cheek diameter of 74 mm and having a symmetrical configuration. The skin of the fruit exhibits a Light Red (Plate 1-E-10) to Dark Red (Plate 4-I-10) blush on a Cream-colored (Plate 17-E-1) ground color. Some light color striping parallel to the ventral suture and on the dorsal side is seen. The ventral suture is Dark Red (Plate 4-K-10). The flesh of the fruit is white to slightly Pink (Plate 4-B-8) with some Red coloration (Plate 4-L-8) at the pit cavity.

BRIEF DESCRIPTION OF THE DRAWING

The accompanying drawing is a color photograph of two mature fruit of the subject variety, one of which has been divided in the suture plane to show the flesh, stone and pit cavity characteristics, together with a twig bearing representative leaves.

DETAILED DESCRIPTION

Referring more specifically to the pomological details of this new and distinct variety of peach tree, the following has been observed under the ecological conditions prevailing in the designated orchard in Reedley, Calif. All major color code plate identifications are by reference to the *Dictionary of Color,* by A. Maerz and M. Paul, Second Edition, published in 1950.

TREE

Vigor: Vigorous.
Productivity: Productive.
Regularity of bearing: Regular.
Branches:
- *Size.*—Medium.
- *Surface texture.*—Medium.
- *Color.*—Older shoots — Reddish-brown (Plate 5-H-10); Young shoots — Light Green (Plate 17-G-5).

Leaves:
- *Size.*—Medium.
- *Length.*—13.5 cm, average.
- *Width.*—3.5 cm, average.

*Shape.*—Lanceolate.
*Color.*—Upper surface — Green (Plate 23-J-6). Lower surface — Light Green (Plate 21-F-4) with light yellow-green midrib vein (Plate 17-G-2).
*Marginal form.*—Crenate.
*Petiole.*—Length — 9 mm, average; thickness — 1 to 1.5 mm.
*Stem glands.*—Number — 3 to 5.
*Arrangement.*—Usually alternate.
*Size.*—Medium.
*Type.*—Reniform.
*Color.*—Light Green (Plate 18-I-4) when young, becoming darker with age.
*Stipules.*—Present, early deciduous.

Flower buds:
*Size.*—Medium.
*Shape.*—Conical.
*Surface.*—Pubescent.

FRUIT

Maturity:
*First pick in* 1983.—August 16.
*Last pick in* 1983.—August 21.

Size: Medium to large.
*Average cheek diameter.*—74 mm.
*Average suture diameter.*—77 mm.
*Average axial diameter.*—71 mm.

Form:
*Symmetry.*—Symmetrical, uniform.
*Suture.*—Distinct, slightly raised and calloused, band averaging 6 mm in width, extending from apex to base.
*Color of suture.*—Moderately Dark Red (Plate 4-K-10).
*Ventral surface.*—Smooth across surface, not lipped.
*Stem cavity.*—Broad, average length — 33 mm; average width — 21 mm; oval in outline.
*Base.*—Rounded at right angle to fruit axis.
*Apex.*—Depressed.
*Pistil point.*—Apical.
*Stem.*—Size — Medium. Average length — 9 mm. Average thickness — 3 to 4 mm.

Skin:
*Thickness.*—Average.
*Texture.*—Average.
*Tendency to crack.*—None observed.
*Color.*—Cream (Plate 17-E-1) covering an average of 15 to 20 percent of surface.
*Blush.*—Light Red (Plate 1-D-10) to Dark Red (Plate 4-I-10). Color both washed and mottled in pattern. Some light color striping parallel to ventral suture and on dorsal side.
*Pubescence.*—Light, short.

Flesh:
*Color.*—White to slightly Pink (Plate 4-B-8) with Red coloration (Plate 4-L-8) at pit cavity. Red coloration radiating from suture line to center of fruit.
*Amygdalin.*—Lacking.
*Juice.*—Moderate.
*Flavor.*—Sweet, low acid.
*Aroma.*—Slight.
*Texture.*—Firm, crisp.
*Fibers.*—Numerous, white, moderately long.
*Ripening.*—Ripens first along suture.
*Eating quality.*—Good.

Stone:
*Adhesion.*—Full freestone.
*Fibers.*—Few.
*Size.*—Medium; average length — 28 mm; average width — 25 mm; average thickness — 20 mm.
*Form.*—Oval to very slightly obovate.
*Base.*—Slightly truncated.
*Sides.*—Nearly equal.
*Ridges.*—Rounded, stronger along ventral suture at mid-stone.
*Grooves.*—Moderate in number over basal shoulder converging basally.
*Color.*—Dark Brown (Plate 7-H-10) with slight purplish tinge.
*Splitting tendency.*—None.

Use: Fresh market for local or long distance shipping.
Keeping quality: Good.
Shipping quality: Not yet shipped in any quantity.
Resistance to disease: No particular susceptibilities noted.

Although the new variety of peach tree possesses the described characteristics under the growing conditions prevailing in Fresno County, Calif., in the central portion of the San Joaquin Valley, it is to be understood that variations of the usual magnitude in characteristics incident to changes in growing conditions, fertilization, pruning and pest control are to be expected.

Having thus described and illustrated my new variety of peach tree, what I claim as new and desire to secure by Plant Letters Patent is:

1. A new and distinct variety of peach tree, substantially as illustrated and described, characterized by its bearing of freestone fruit having white flesh and by its general resemblance to the Giant Babcock Peach Tree (U.S. Plant Pat. No. 1,353) from which it is distinguished by its bearing of fruit maturing approximately one month later than that of the Giant Babcock and having a distinctive suture having a dark red coloration radiating through the flesh in the suture plane toward the stone.

* * * * *